US012714291B2

(12) United States Patent
Iwasaki

(10) Patent No.: US 12,714,291 B2
(45) Date of Patent: Aug. 25, 2026

(54) CHANNEL REPLACEMENT METHOD, ENDOSCOPE, AND PLUG

(71) Applicant: OLYMPUS MEDICAL SYSTEMS CORP., Tokyo (JP)

(72) Inventor: Seiji Iwasaki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 355 days.

(21) Appl. No.: 18/230,709

(22) Filed: Aug. 7, 2023

(65) Prior Publication Data

US 2024/0049947 A1 Feb. 15, 2024

Related U.S. Application Data

(60) Provisional application No. 63/397,917, filed on Aug. 15, 2022.

(51) Int. Cl.

*A61B 1/00* (2006.01)
*A61B 1/018* (2006.01)
*A61B 1/12* (2006.01)

(52) U.S. Cl.

CPC ...... *A61B 1/00137* (2013.01); *A61B 1/00105* (2013.01); *A61B 1/0011* (2013.01); *A61B 1/018* (2013.01); *A61B 1/122* (2013.01)

(58) Field of Classification Search

CPC . A61B 1/0011; A61B 1/00119; A61B 1/0014; A61B 1/00142; A61B 1/00105; A61B 1/121; A61B 1/00112; A61B 1/00071; A61B 1/12; A61B 1/122

See application file for complete search history.

(56) References Cited

U.S. PATENT DOCUMENTS 4,771,766 A * 9/1988 Aoshiro ................. A61B 1/121 600/155
2018/0333044 A1* 11/2018 Jenkins .............. A61B 1/00059

FOREIGN PATENT DOCUMENTS

JP 2005-318982 A 11/2005

* cited by examiner

*Primary Examiner* — Sarah W Aleman
(74) *Attorney, Agent, or Firm* — Morgan, Lewis & Bockius LLP

(57) ABSTRACT

A channel replacement method to replace a first channel of an endoscope, the first channel including a first distal end and a first rear end, the channel replacement method including: sealing a flow path of the first channel by arranging a first plug at the first distal end and arranging a second plug at the first rear end, and withdrawing the first channel from inside the endoscope.

19 Claims, 16 Drawing Sheets

CHANNEL REPLACEMENT METHOD, ENDOSCOPE, AND PLUG

RELATED APPLICATION DATA

This application is based on and claims priority under 35 U.S.C. § 119 to U.S. Provisional Application No. 63/397,917 filed on Aug. 15, 2022, the entire contents of which are incorporated herein by reference.

FIELD OF DISCLOSURE

The present disclosure relates to a replacement method of a channel of an endoscope, an endoscope including a channel, a plug for stopping up an opening of a channel of an endoscope, and a channel withdrawal method.

BACKGROUND

An endoscope is used to observe a region that is not visible from the outside by inserting an elongated insertion portion of the endoscope into a subject. In addition, a treatment instrument such as a forceps is inserted into a forceps channel which is inserted through the insertion portion, and treatment is performed using the treatment instrument that protrudes from an opening of a distal end portion of the insertion portion. The endoscope is periodically inspected and repair work including replacement of the channel may be performed.

Recently, single-use endoscopes which are disposed of after a single use are being used. Even single-use endoscopes may be collected after use to be cleaned, inspected, and repaired by the manufacturer to be reused in the interest of economically using resources.

When reusing single-use endoscopes, replacement processing of a channel can be considered in place of cleaning of the channel.

Japanese Patent Application Laid-Open Publication No. 2005-318982 discloses a channel replacement method in which a new channel is inserted into an endoscope by, first, fitting a rear end of the new channel into a distal end of an old channel and, next, withdrawing the old channel from inside the endoscope.

SUMMARY

A channel replacement method to replace a first channel according to an embodiment includes: sealing a flow path of the first channel by arranging a first plug at a first distal end of the first channel and arranging a second plug at a first rear end of the first channel, and withdrawing the first channel from inside the endoscope.

An endoscope according to an embodiment includes: an insertion portion, an operation portion arranged proximally relative to the insertion portion, and a channel including a main channel that includes a distal end located in a first opening of the insertion portion and a rear end located in a second opening of the operation portion. The second opening is large enough to withdraw the channel to an outside via the second opening.

A plug according to an embodiment is a plug which stops up an opening of a channel of an endoscope. The plug includes an adhesive for fixing the plug to the opening.

DETAILED DESCRIPTION

Hereinafter, embodiments of the present disclosure will be described based on the drawings.

Note that the drawings based on the embodiments are schematic in nature. A relationship between a thickness and a width in each portion of the drawings, a ratio of thicknesses among respective portions, and the like differ from reality. Furthermore, even among the drawings, the drawings include portions having a relationship or a ratio among dimensions that differ from each other. Illustration and assignment of reference signs with respect to a part of the components will be omitted.

First Embodiment

Figure 1:
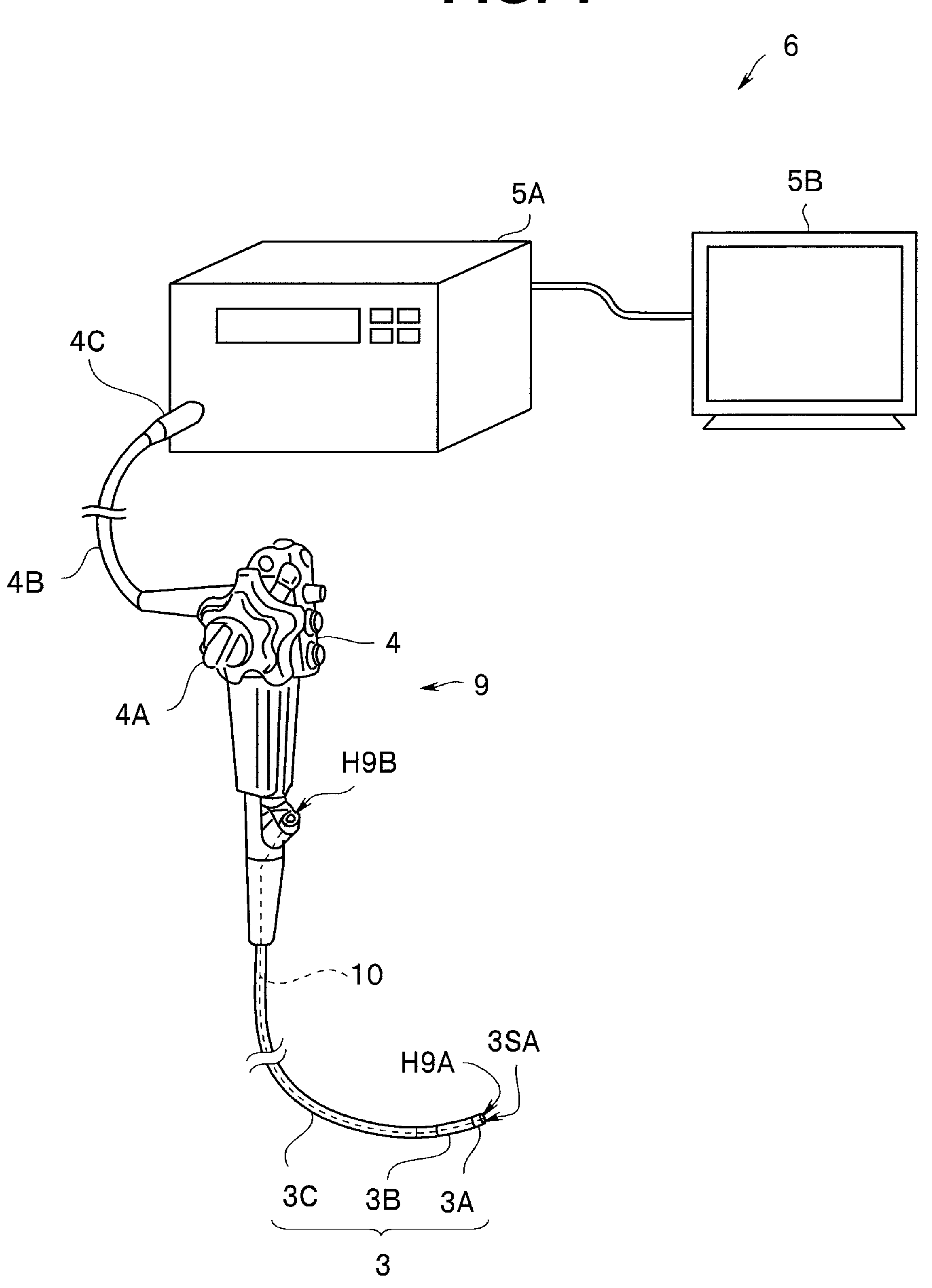
FIG. 1 is a perspective view of an endoscope system including an endoscope according to a first embodiment.

An endoscope 9 according to the present embodiment shown in FIG. 1 constitutes an endoscope system 6 together with a video processor 5A and a monitor 5B.

The endoscope 9 includes an insertion portion 3, an operation portion 4, a universal cord 4B, and a connector 4C. The insertion portion 3 is to be inserted into the body of a subject. The operation portion 4 is arranged proximally relative to the insertion portion 3. The universal cord 4B is extended from the operation portion 4. The connector 4C is arranged at a proximal end of the universal cord 4B. The universal cord 4B is extended from the operation portion 4, and the connector 4C is arranged proximally relative to the universal cord 4B.

In the insertion portion 3, a distal end portion 3A on a distal end side, a bending portion 3B which is arranged on a proximal end side of the distal end portion 3A, and an elongated soft tube 3C which connects a proximal end side of the bending portion 3B and the operation portion 4 to each other are consecutively provided. The bending portion 3B bends in accordance with an operation of a bending knob 4A of the operation portion 4.

The video processor 5A including a CPU processes an image pickup signal outputted by the endoscope 9 and transmits an image signal to the monitor 5B. The monitor 5B displays an endoscopic image. The video processor 5A includes a light source circuit which generates illuminating light or the like. The light source circuit may be included in a light source unit which is separate from the video processor 5A.

A channel 10 is arranged inside the endoscope 9. The channel 10 is inserted from an insertion opening (second opening) H9B of the operation portion 4 to a projection opening (first opening) H9A of a distal end surface 3SA of the distal end portion 3A. Although not illustrated, a treatment instrument inserted from the insertion opening H9B protrudes from the projection opening H9A.

Figure 2:
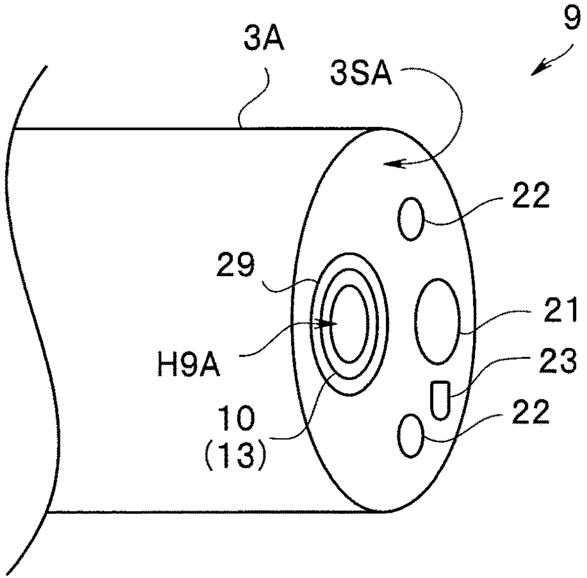
FIG. 2 is a perspective view of a distal end portion of the endoscope according to the first embodiment.

As shown in FIG. 2, an observation window 21, an illumination window 22, and a cleaning nozzle 23 of an image pickup unit are provided on the distal end surface 3SA of the distal end portion 3A. A distal end 13 of the channel 10 is fixed to the projection opening H9A of the distal end surface 3SA using a fixing member 29 such as an adhesive. The fixing member 29 attaches the channel 10 to the opening of the insertion portion 3.

Figure 3:
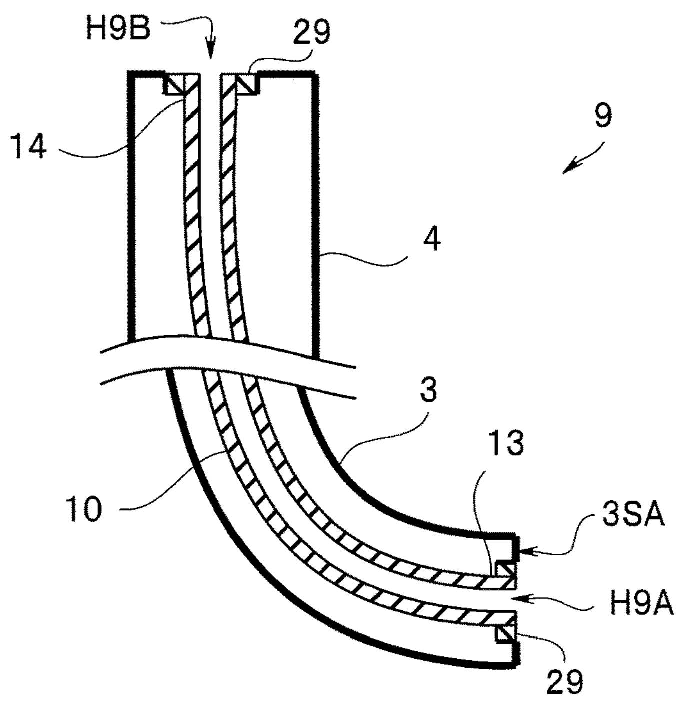
FIG. 3 is a schematic cross-sectional view of a channel of the endoscope according to the first embodiment.

FIG. 3 is a schematic cross-sectional view of the channel 10 of the endoscope 9. The distal end 13 of the channel 10 is fixed to the projection opening H9A of the insertion portion 3 using the fixing member 29. A rear end 14 of the channel 10 is fixed to the insertion opening H9B of the operation portion 4 using the fixing member 29. The distal end 13 of the channel 10 and the rear end 14 of the channel 10 may be fixed using different fixing members 29.

Although the endoscope 9 is a single-use endoscope, the endoscope 9 is subjected to cleaning by a manufacturer after use to be reused. Note that cleaning in the present specification refers to rinsing by water, cleaning using a solvent for removing contaminants such as organic substances, disinfection for neutralizing microorganisms, sterilization for eliminating or killing microorganisms, or a combination of these types of processing.

Cleaning of an outer surface of the endoscope 9 is relatively easy. However, cleaning of a flow path of the channel 10 is not easy. Replacing an old channel of an endoscope after use with a new channel with same specifications enables a single-use endoscope to be readily reused. Hereinafter, the old channel after use of which a flow path is potentially contaminated will be referred to as a "first channel" and the new channel which is unused will be referred to as a "second channel". The endoscope is a single-use endoscope.

In addition, in the description of the channel 10 of an endoscope 9A, "A" will be added to reference signs of components of the first channel (old channel) and "B" will be added to reference signs of components of the second channel (new channel). For example, the reference sign of the first channel is "10A" and the reference sign of the second channel is "10B".

Figure 4:
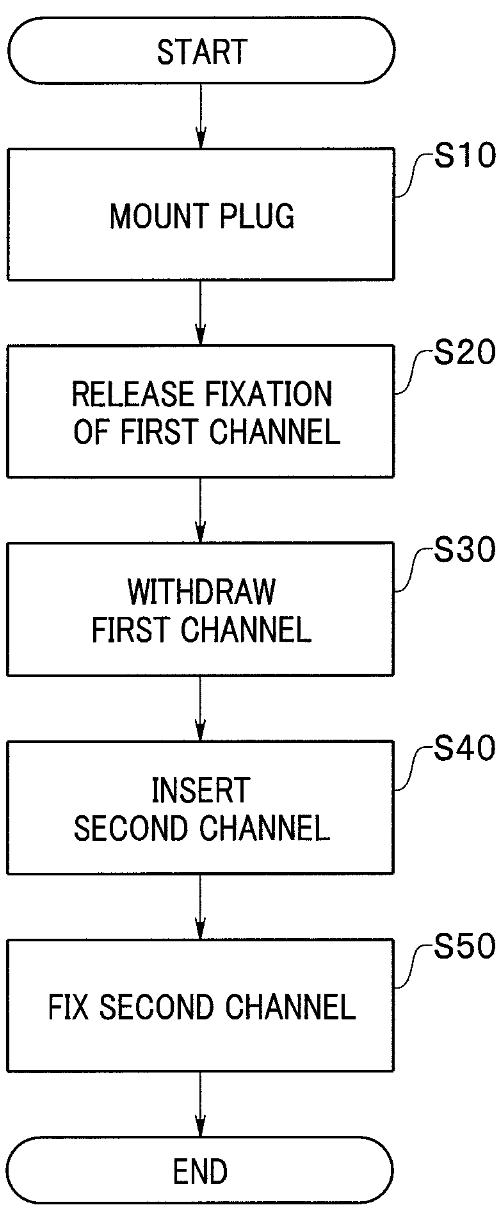
FIG. 4 is a flow chart of a channel replacement method according to the first embodiment.

Hereinafter, a channel replacement method of an endoscope will be described according to the flow chart shown in FIG. 4. FIG. 4 shows the channel replacement method to replace the first channel 10A of the endoscope 9, and the withdrawal method of the first channel 10A of the endoscope 9.

For example, the endoscope 9 after use is sealed in a bag and collected. An outer surface of the collected endoscope 9 is subjected to cleaning by a manufacturer. A flow path of the first channel 10A can be easily cleaned at the same time as the cleaning of the outer surface.

<Step S10> Mounting of Plug

Figure 5:
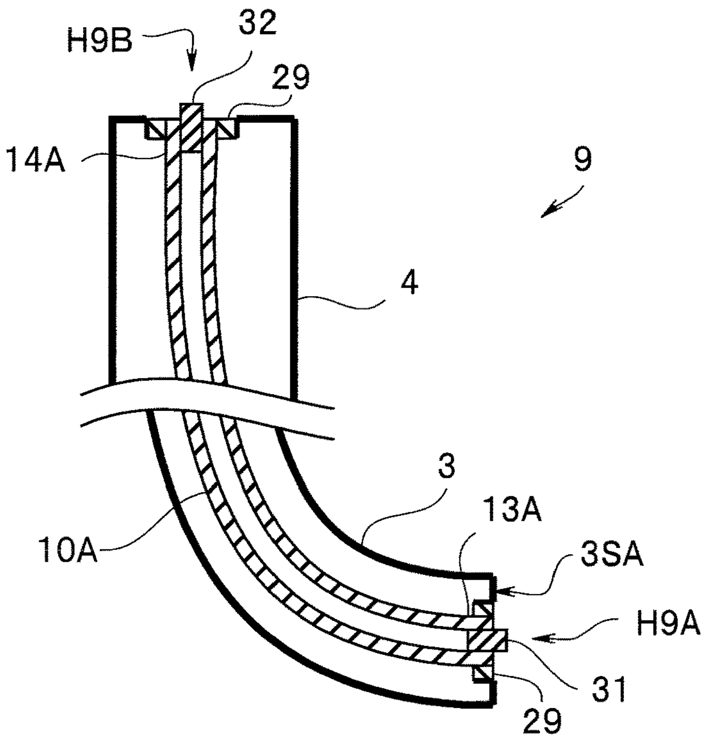
FIG. 5 is a schematic cross-sectional view for describing a replacement method of a channel according to the first embodiment.

As shown in FIG. 5, a first plug 31 is arranged at a first distal end 13A and a second plug 32 is arranged at a first rear end 14A. The flow path of the first channel 10A is sealed by the first plug 31 and the second plug 32. The first channel 10A includes the first distal end 13A and the first rear end 14A. The channel replacement method includes sealing the flow path of the first channel 10A by arranging the first plug 31 at the first distal end 13A and arranging the second plug 32 at the first rear end 14A.

The channel 10 can include a main channel 11M that includes the distal end 13A located in the first opening H9A of the insertion portion 3 and the rear end 14A located in the second opening H9B of the operation portion 4. The insertion opening H9B is large enough to withdraw the channel to an outside via the insertion opening H9B.

Hereinafter, each of a plurality of plugs (for example, the first plug 31 and the second plug 32) will be referred to as a plug 30. The plug 30 with a cylindrical shape has an outer diameter which is slightly larger than a flow path diameter of the channel. For example, the plug 30 which is made of an elastic resin such as silicone resin or rubber is pressed into an opening of the first channel 10A.

Note that the endoscope 9 may be collected after a user seals the flow path of the first channel 10A with the plug 30 immediately after use.

<Step S20> Release of Fixation of First Channel

Figure 6:
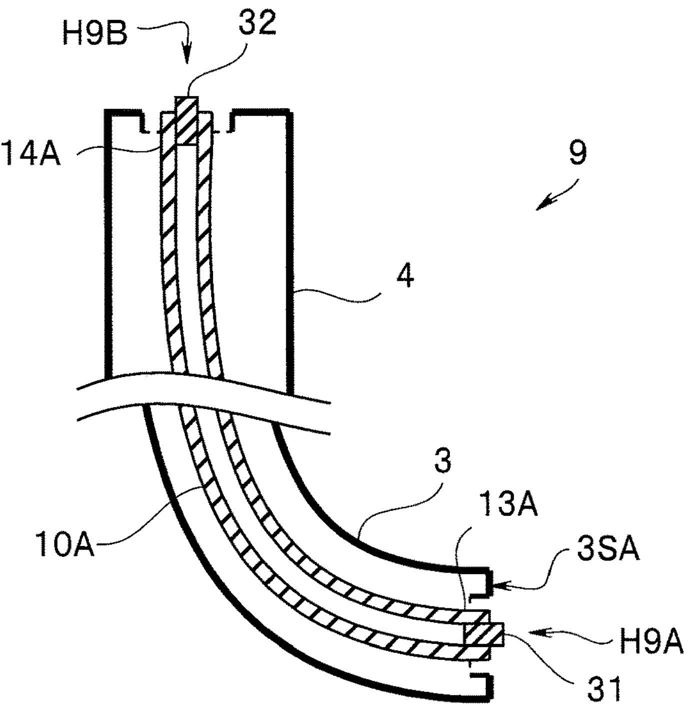
FIG. 6 is a schematic cross-sectional view for describing the replacement method of a channel according to the first embodiment.

As shown in FIG. 6, fixation of the first channel 10A to the endoscope 9 is released. For example, the fixing member 29 fixing the first distal end 13A of the first channel 10A to the projection opening H9A is grinded off using a drill. In addition, the fixing member 29 fixing the first rear end 14A to the insertion opening H9B is grinded off. The fixing member 29 attaches the channel 10A to the opening of the insertion portion 3. The method includes removing the fixing member 29 before withdrawing the first channel 10A from inside the endoscope 9.

Note that the plug 30 may be arranged after releasing the fixation of the first channel 10A. In other words, step S20 may be performed before step S10.

<Step S30> Withdrawal of First Channel

Figure 7:
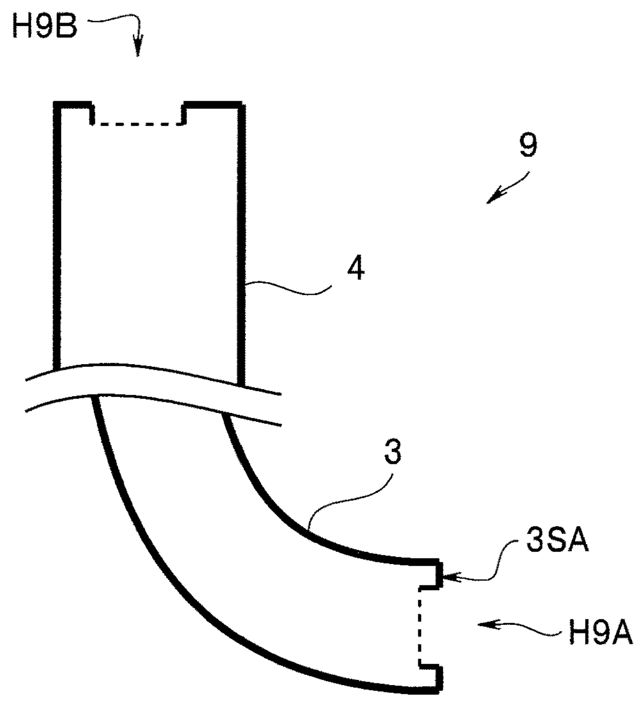
FIG. 7 is a schematic cross-sectional view for describing the replacement method of a channel according to the first embodiment.

As shown in FIG. 7, the first channel 10A is withdrawn from inside the endoscope 9 via the projection opening H9A or the insertion opening H9B. The channel replacement method includes withdrawing the first channel 10A from inside the endoscope 9.

<Step S40> Insertion of Second Channel

Figure 8:
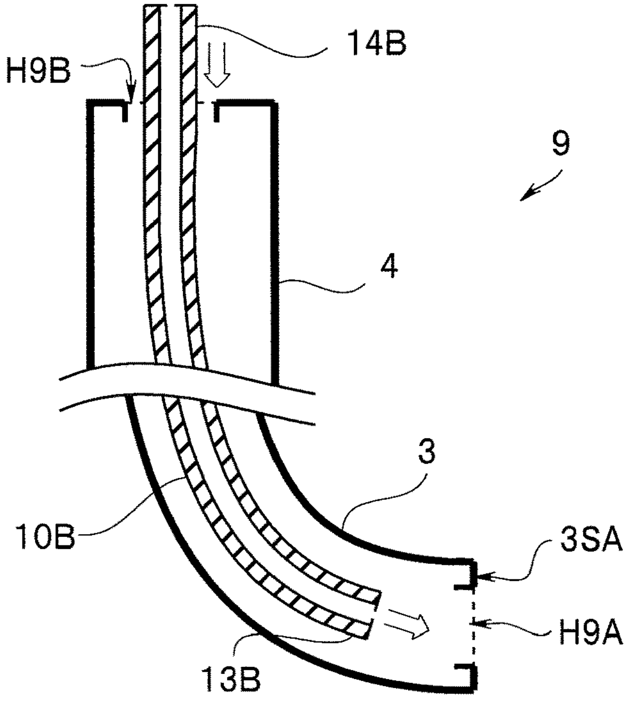
FIG. 8 is a schematic cross-sectional view for describing the replacement method of a channel according to the first embodiment.

As shown in FIG. 8, the second channel 10B is inserted into the endoscope 9 via the insertion opening H9B. The second channel 10B is a new channel or, in other words, an unused channel and a flow path of the second channel 10B is not contaminated. Obviously, the second channel 10B can be inserted into the endoscope 9 via the projection opening H9A. The channel replacement method includes after withdrawing the first channel 10A, inserting the second channel 10B into the endoscope 9 such that the second channel 10B occupies a space within the endoscope 9 previously occupied by the first channel 10A. The inserting the second channel 10B into the endoscope 9 can include inserting the second channel 10B into the endoscope 9 from a rear side of the insertion portion 3 toward a distal side of the insertion portion 3.

<Step S50> Fixation of Second Channel

Although not illustrated, a second distal end 13B of the second channel 10B is fixed to the projection opening H9A using a fixing member. A second rear end 14B of the second channel 10B is fixed to the insertion opening H9B using a fixing member. The second channel 10B includes the second distal end 13B and the second rear end 14B.

While a single-use endoscope has been described above as an example, it goes without saying that even with multi-use endoscopes of which reuse is a regular mode, channel replacement can be performed in an efficient manner by a process similar to the process for single-use endoscopes.

With the channel replacement method according to the present embodiment, a single-use endoscope can be readily reused. In addition, with the plug 30, contaminants remaining in the flow path of the old channel are prevented from flowing out during replacement work. In particular, since contamination of the new channel can be prevented, the new channel can be used without cleaning after replacement. Furthermore, the old channel can be readily withdrawn from inside the endoscope 9 using the plug 30. Therefore, the channel replacement method according to the present embodiment is efficient. The endoscope 9 can be applied to, for example, the single-use endoscope to be disposed of after being used once, but may be a re-use endoscope to be repeatedly used.

As described above, an object of the embodiments of the present disclosure is to provide an efficient channel replacement method, an endoscope which enables a channel to be efficiently replaced, and a plug for performing efficient channel replacement. In addition, with the embodiments of the present disclosure, an efficient channel replacement method, an endoscope which enables a channel to be efficiently replaced, and a plug for performing efficient channel replacement can be provided.

Note that the plug 30 for stopping up the opening of the channel 10 and sealing the flow path is not limited to a cylindrical shape.

Figure 9A:
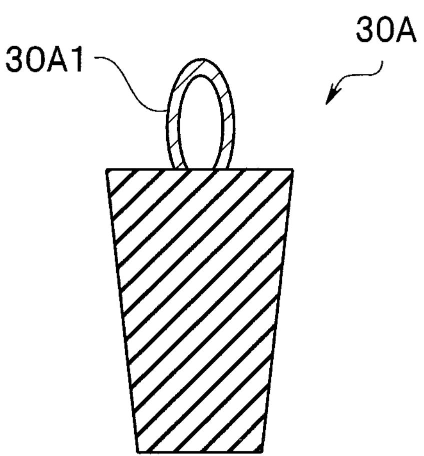
FIG. 9A is a cross-sectional view of a plug of an example of the endoscope according to the first embodiment.

An outer diameter of a plug 30A shown in FIG. 9A decreases toward a distal end. The plug 30A can be more readily inserted into the opening of the channel 10 than the plug 30. In addition, the plug 30A is provided with a ring 30A1 made of, for example, metal. Therefore, the plug 30A is readily grasped or a string can be readily attached to the plug 30A.

Figure 9B:
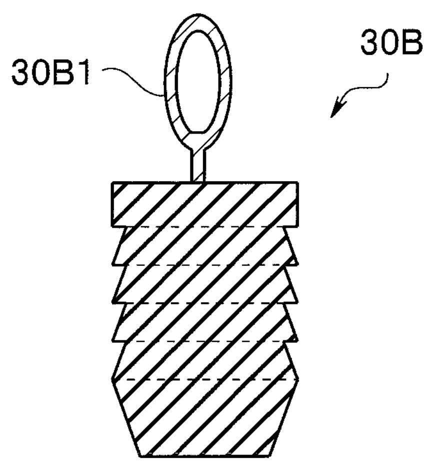
FIG. 9B is a cross-sectional view of a plug of an example of the endoscope according to the first embodiment.

An inversely tapered groove is formed on an outer peripheral surface of a plug 30B shown in FIG. 9B. The plug 30B is less likely to fall out after insertion into the channel than the plug 30. The plug 30B is provided with a ring 30B1.

Figure 9C:
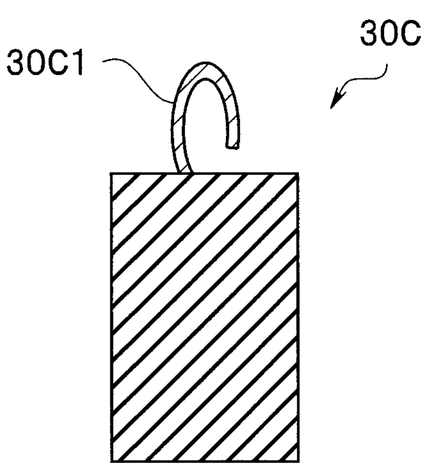
FIG. 9C is a cross-sectional view of a plug of an example of the endoscope according to the first embodiment.

A plug 30C shown in FIG. 9C is provided with a hook 30C1 which has an approximately C-shape. The plug 30C including the hook 30C1 can be connected to a plug with a same configuration without having to use another member such as a string.

Figure 9D:
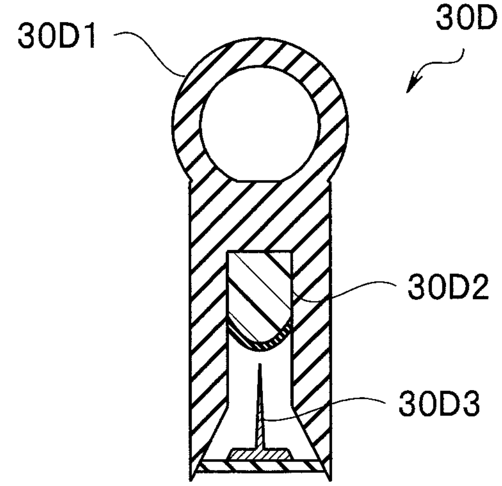
FIG. 9D is a cross-sectional view of a plug of an example of the endoscope according to the first embodiment.

A plug 30D shown in FIG. 9D includes an adhesive 30D2 for fixing the plug 30D to the channel and for completely filling a gap between the plug 30D and the channel. For example, the adhesive 30D2 is arranged in a state of being sealed in a bag in a hollow portion of the plug 30D. When the plug 30D is pressed into the channel, a needle member 30D3 is pushed into the hollow portion, the bag containing the adhesive 30D2 is punctured, and the adhesive 30D2 flows out. For example, the plug 30D is fixed to the channel as the adhesive 30D2 reacts with moisture in air and hardens. With the channel to which the plug 30D is fixed by the adhesive 30D2, since the plug 30D cannot be withdrawn, there is no risk of erroneous reuse.

In addition, with the plug 30D, a part of the plug body has a ring shape. The plug 30D can be readily manufactured because the plug may not have another member for attaching a string. The plug (30A, 30B, 30C or 30D) stops up the opening of the channel 10 of an endoscope 9, the plug can include the adhesive for fixing the plug to the opening.

As long as the flow path of the channel can be sealed, a plug (cap) structured to come into close contact with the outer peripheral surface of the channel can be arranged at an end portion of the channel.

Modification of First Embodiment

A channel replacement method according to the present modification is similar to the channel replacement method according to the first embodiment and produces a same effect. Therefore, in the following description, components with same functions as the channel according to the first embodiment will be assigned same reference signs and descriptions of such components will be omitted.

First Modification of First Embodiment

Figure 10:
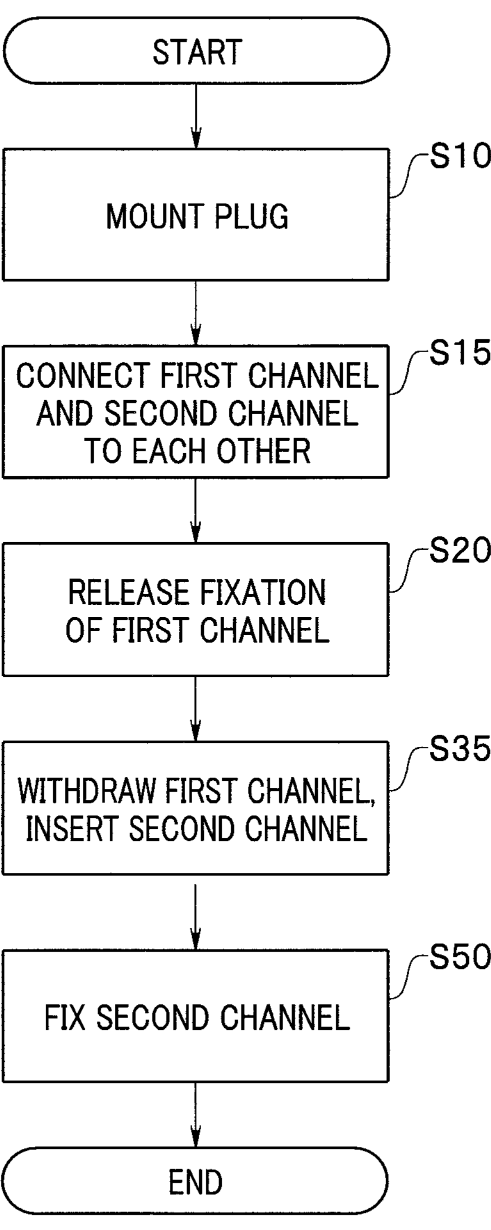
FIG. 10 is a flow chart of a channel replacement method according to a modification of the first embodiment.

The channel replacement method according to the present modification will be described according to the flow chart shown in FIG. 10. In the channel replacement method according to the present modification, a second channel 10B is inserted into the endoscope 9 due to the withdrawal of a first channel 10A.

<Step S10> Mounting of Plug

The step is the same as step S10 in FIG. 4. Note that a plug 33 is further arranged at a second distal end 10B1 of the second channel 10B. A plug 34 may be further arranged at the second rear end 14B for the purpose of preventing contamination of the second channel 10B during replacement work.

<Step S15> Connection of First Channel and Second Channel

Figure 11:
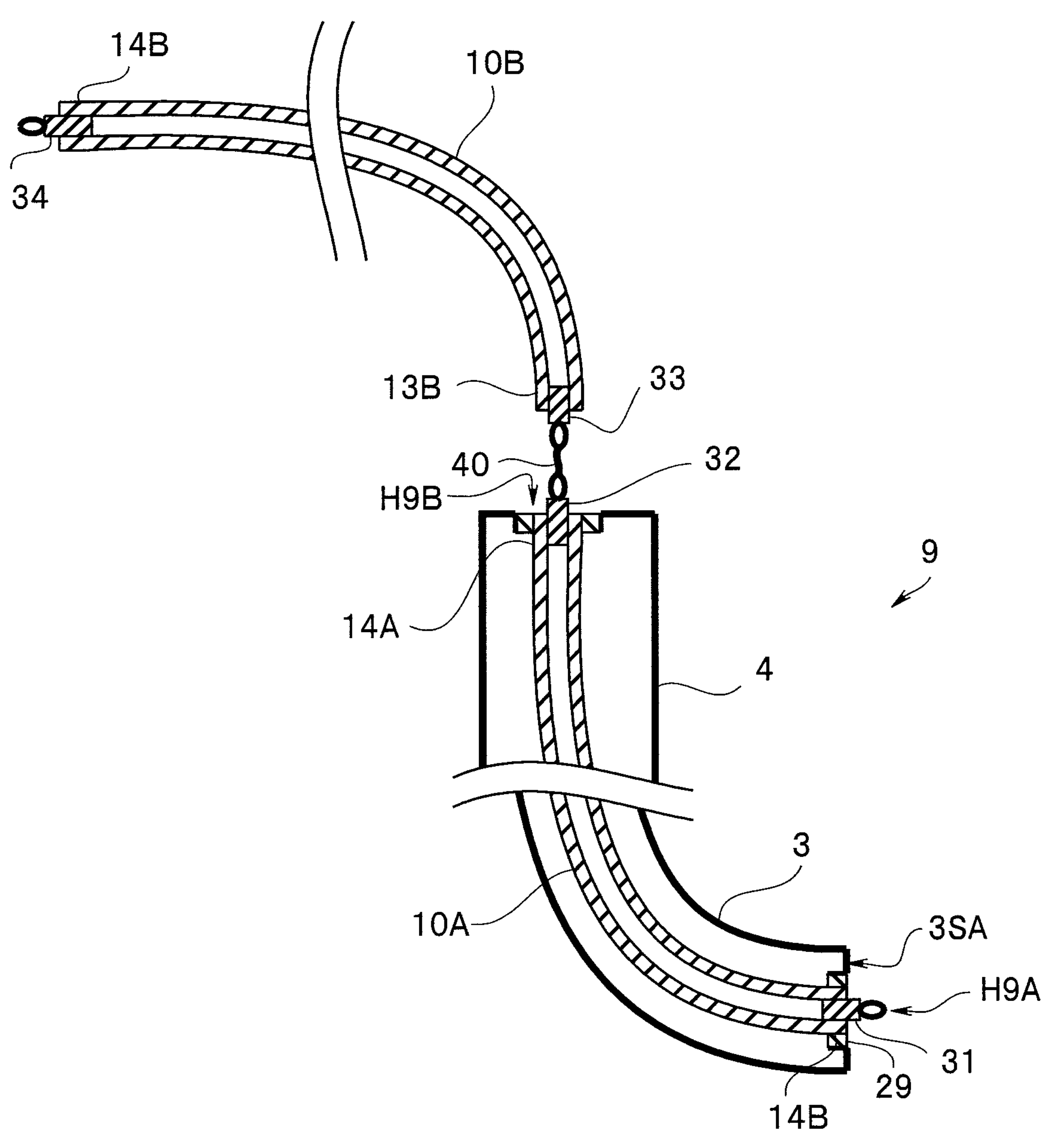
FIG. 11 is a schematic cross-sectional view for describing a replacement method of a channel according to a modification of the first embodiment.

As shown in FIG. 11, the first rear end 14A of the first channel 10A and the second distal end 13B of the second channel 10B are mechanically connected to each other. For example, the second plug 32 of the first rear end 14A and the plug 33 of the second distal end 13B are connected to each other using a string (line) 40. When using the plug 30 including a hook (for example, the plug 30C shown in FIG. 9C), two plugs 30 may be connected to each other without using a string. Withdrawing the first channel 10A from inside the endoscope 9 and inserting the second channel 10B into the endoscope includes mechanically connecting the first rear end 14A and the second distal end 13B or the first distal end 13A and the second rear end 14B to each other, and inserting the second channel 10B into the endoscope 9 by withdrawing the first channel 10A from inside the endoscope 9. The channel replacement method includes connecting the line 40 to the first plug 31 or the second plug 32.

Note that, in step S15, the first distal end 13A of the first channel 10A and the second rear end 14B of the second channel 10B may be mechanically connected to each other.

<Step S20> Release of Fixation of First Channel

The step is the same as step S20 in FIG. 4. Step S20 may be performed before step S10.

<Step S35> Withdrawal of First Channel/Insertion of Second Channel

Figure 12:
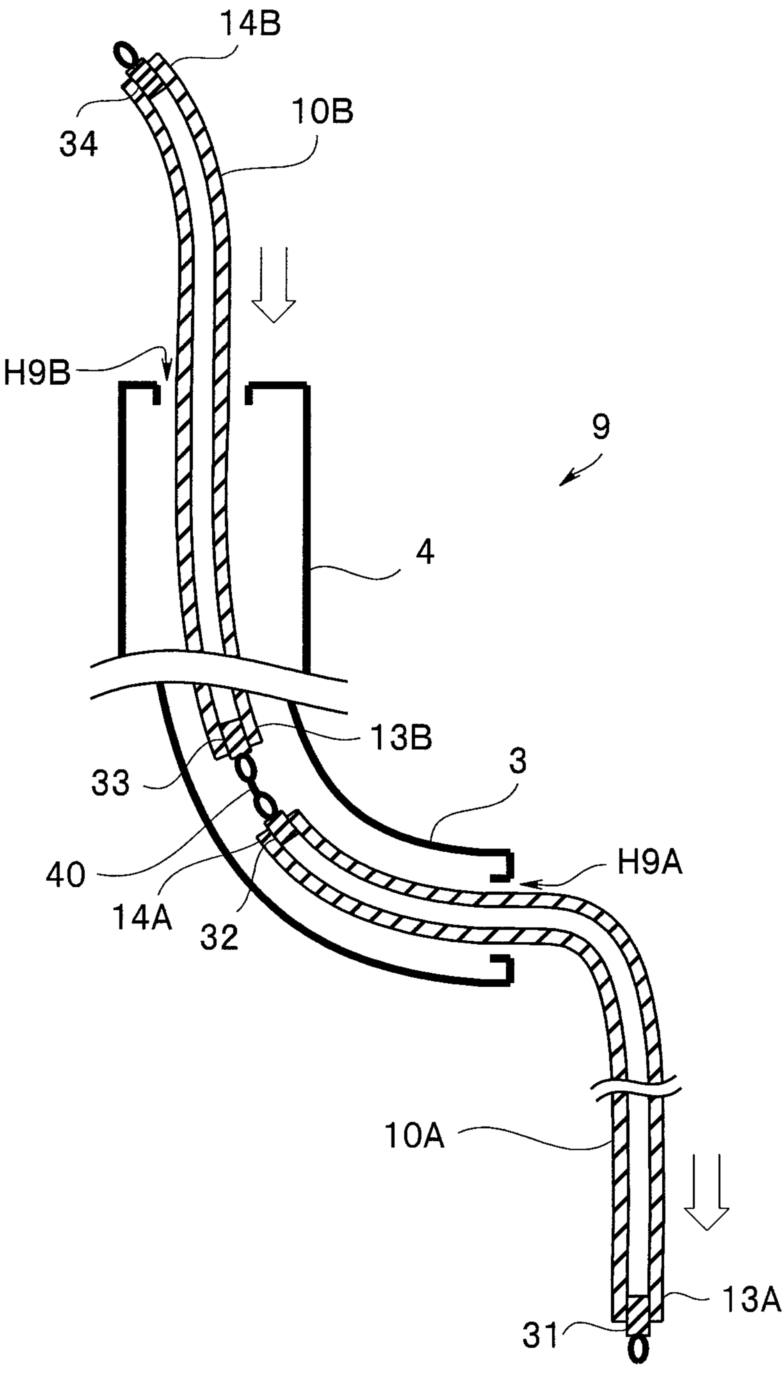
FIG. 12 is a schematic cross-sectional view for describing the replacement method of a channel according to the modification of the first embodiment.

As shown in FIG. 12, when the first channel 10A is withdrawn from inside the endoscope 9 via the projection opening H9A, the second channel 10B is simultaneously inserted into the endoscope 9 via the insertion opening H9B.

Note that in a case where the first distal end 13A of the first channel 10A and the second rear end 14B of the second channel 10B are connected to each other, when the first channel 10A is withdrawn from inside the endoscope 9 via the insertion opening H9B, the second channel 10B is simultaneously inserted into the endoscope 9 via the projection opening H9A. The channel replacement method includes positioning the line 40 inside the endoscope 9 by withdrawing the first channel 10A from inside the endoscope 9, connecting the line 40 to the second distal end 13B or the second rear end 14B of the second channel 10B, and inserting the second channel 10B into the endoscope 9 by pulling the line 40 connected to the second distal end 13B or the second rear end 14B. The line 40 can be, for example, a string, a wire, or any other fiber, plastic, or metal line.

<Step S50> Fixation of Second Channel

The step is the same as step S50 in FIG. 4.

With the channel replacement method according to the present modification, the second channel 10B can be more readily inserted into the endoscope 9 than in the channel replacement method according to the first embodiment.

Second Modification of First Embodiment

In a channel replacement method according to the present modification, a first end 40A of the string 40 is connected to the second plug 32. A length of the string 40 including the first end 40A and a second end 40B is longer than the length of the first channel 10A.

Figure 13:
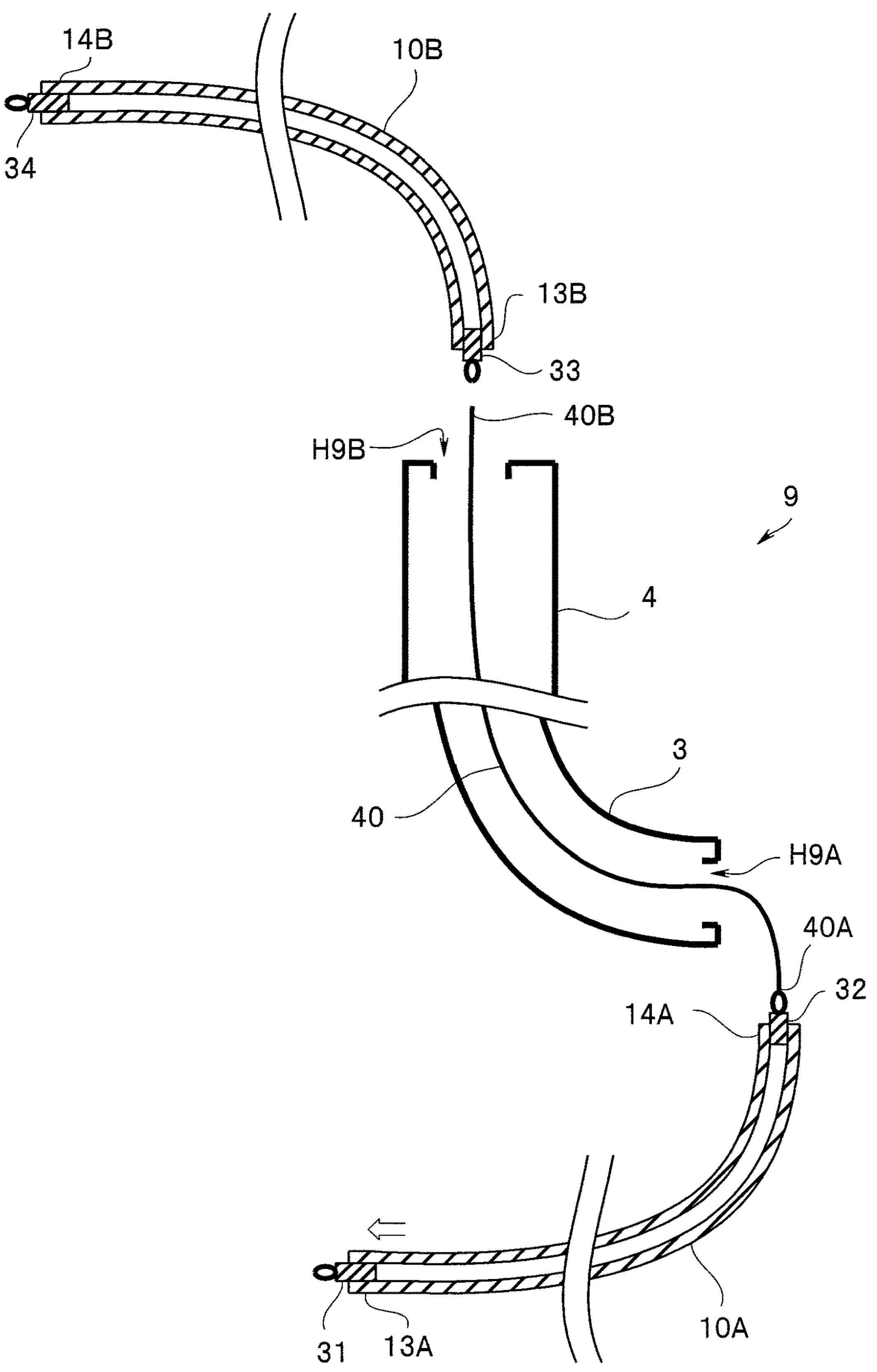
FIG. 13 is a schematic cross-sectional view for describing the replacement method of a channel according to the first embodiment.

As shown in FIG. 13, by withdrawing the first channel 10A from inside the endoscope 9 via the projection opening H9A, the string 40 is placed inside the endoscope 9. In other words, a state is created where the first end 40A and the second end 40B of the string 40 are positioned outside of the endoscope 9. The first end 40A of the string 40 placed in the endoscope 9 is detached from the second plug 32.

The second end 40B of the string 40 is connected to the plug 33 of the second distal end 10B1 of the second channel 10B. Then, by pulling the first end 40A of the string 40, the second channel 10B is inserted into the endoscope via the insertion opening H9B.

Note that the string 40 may be connected to the first plug 31 at the first distal end 13A of the first channel 10A, the first channel 10A1 may be withdrawn from inside the endoscope 9 via the insertion opening H9B, and the second channel 10B may be inserted into the endoscope 9 via the projection opening H9A.

In the channel replacement method according to the present modification, since the first channel 10A is already detached from the string 40 when inserting the second channel 10B into the endoscope 9, workability is further improved as compared to the channel replacement method according to the first modification of the first embodiment. The channel replacement method includes positioning the line 40 inside the endoscope 9 by withdrawing the first channel 10A from inside the endoscope 9, connecting the line 40 to the second distal end 13B or the second rear end 14B of the second channel 10B, and inserting the second channel 10B into the endoscope 9 by pulling the line 40 connected to the second distal end 13B or the second rear end 14B. The line 40 can be, for example, a string, a wire, or any other fiber, plastic, or metal line.

Second Embodiment

An endoscope 9A according to the present embodiment is similar to the endoscope 9 according to the first embodiment and produces a same effect. Therefore, in the following description, components with same functions as the endoscope 9 according to the first embodiment will be assigned same reference signs and descriptions of such components will be omitted.

Figure 14:
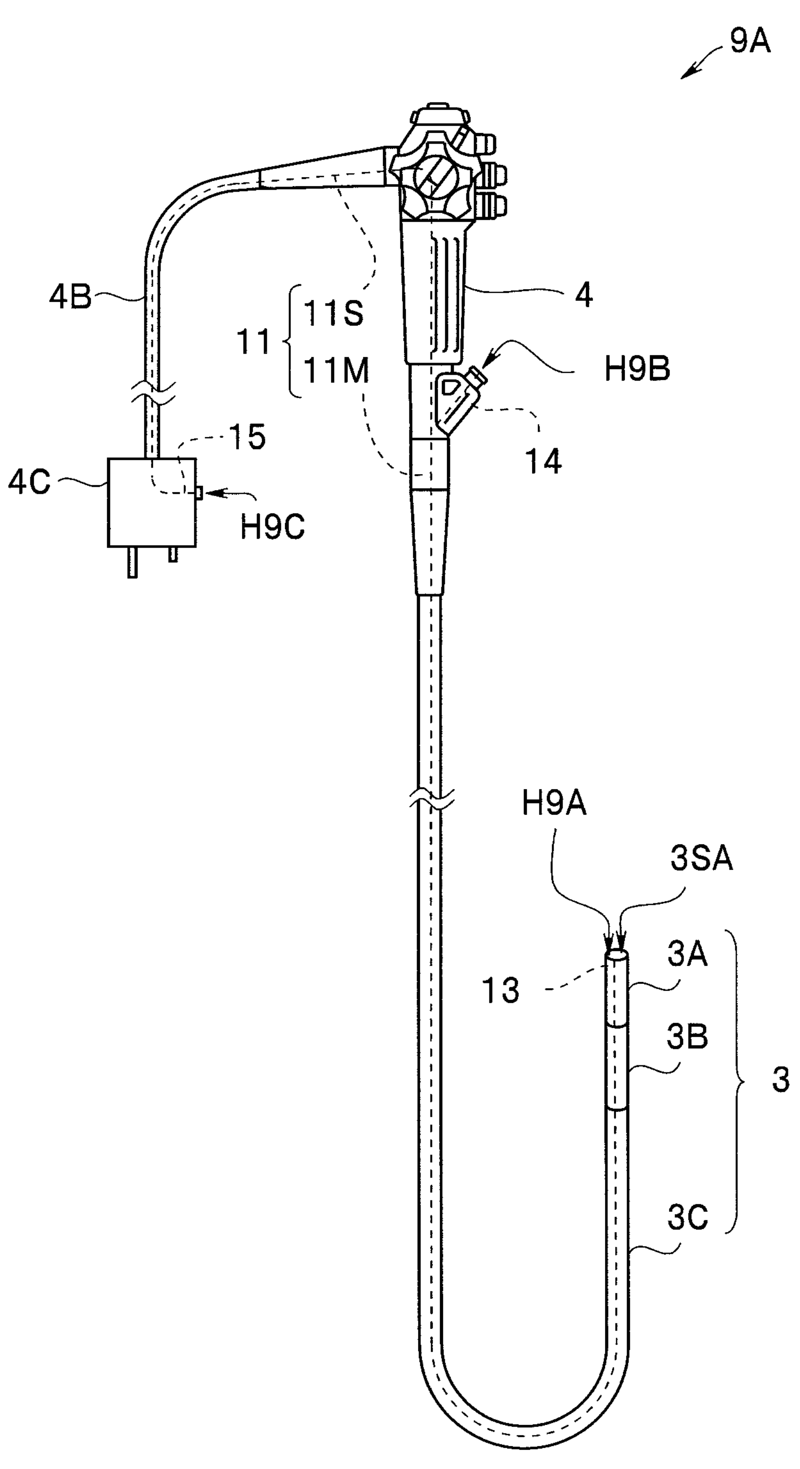
FIG. 14 is a perspective view of an endoscope according to a second embodiment.
Figure 15:
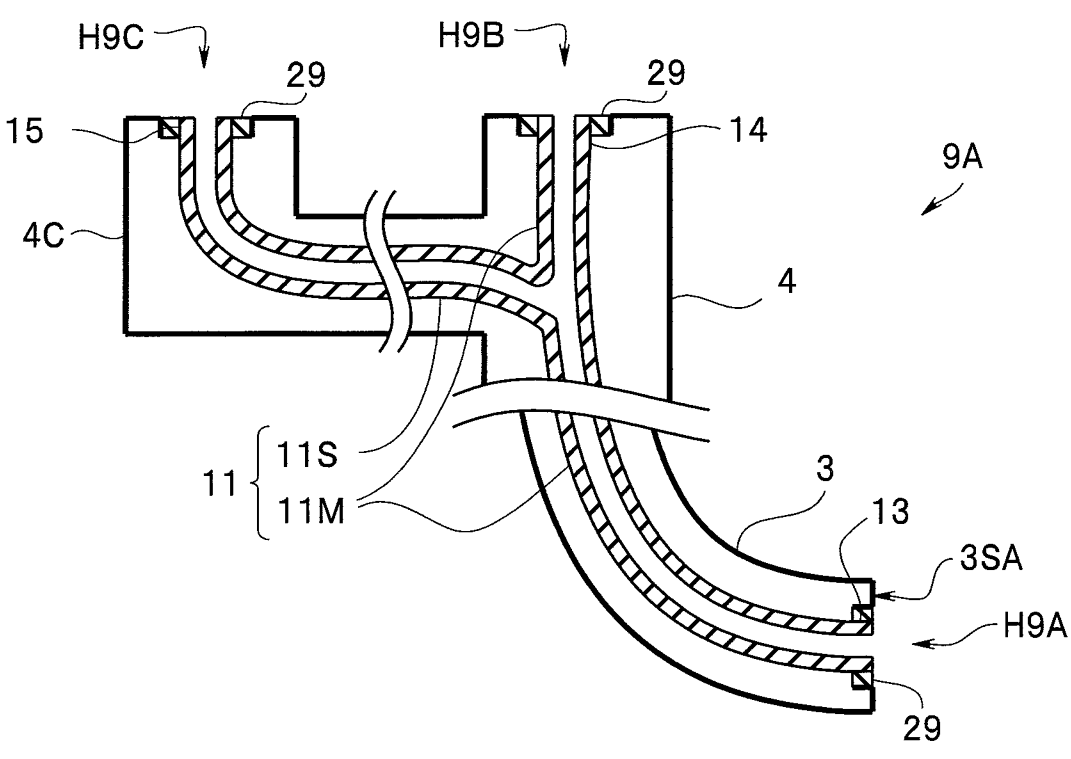
FIG. 15 is a schematic cross-sectional view of a channel of the endoscope according to the second embodiment.

As shown in FIGS. 14 and 15, a channel 11 of the endoscope 9A according to the present embodiment includes the main channel 11M and a subchannel 11S which branches from a middle of the main channel 11M.

The channel 11 includes the distal end 13, the rear end 14, and a branch end 15. In other words, the main channel 11M includes the distal end 13 on the distal end surface 3SA of the insertion portion 3 and the rear end 14 in the operation portion 4. The main channel 11M is a forceps channel which is inserted from the distal end portion 3A to the operation portion 4. The subchannel 11S is a suction channel which branches from the main channel 11M in the operation portion 4, which includes the branch end 15 in the connector 4C, and which is inserted from the operation portion 4 to the connector 4C.

As will be described later, in the endoscope 9A, the insertion opening H9B of the operation portion 4 is designed in a size which enables the channel 11 to be withdrawn.

Figure 16:
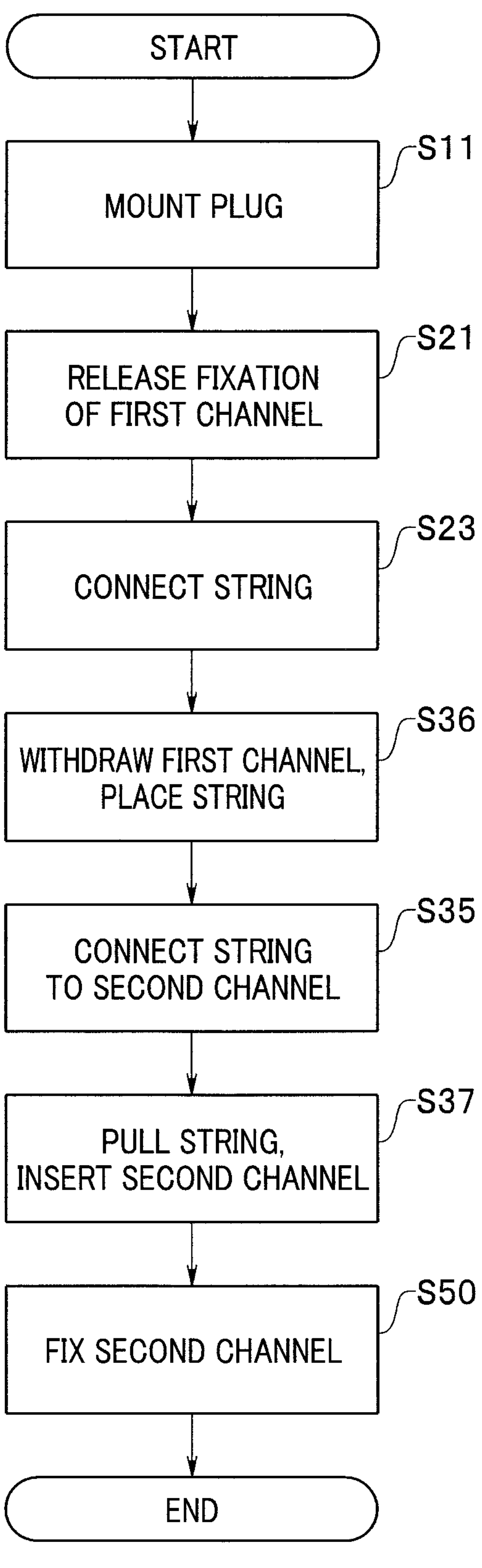
FIG. 16 is a flow chart of a channel replacement method according to the second embodiment.

A channel replacement method of the endoscope 9A will be described according to the flow chart shown in FIG. 16. Hereinafter, in the description of the channel 11 of the endoscope 9A, "A" will be added to reference signs of components of a first channel (old channel) and "B" will be added to reference signs of components of a second channel (new channel). For example, the reference sign of the first channel is "11A" and the reference sign of the second channel is "11B".

<Step S11> Mounting of Plug

Figure 17:
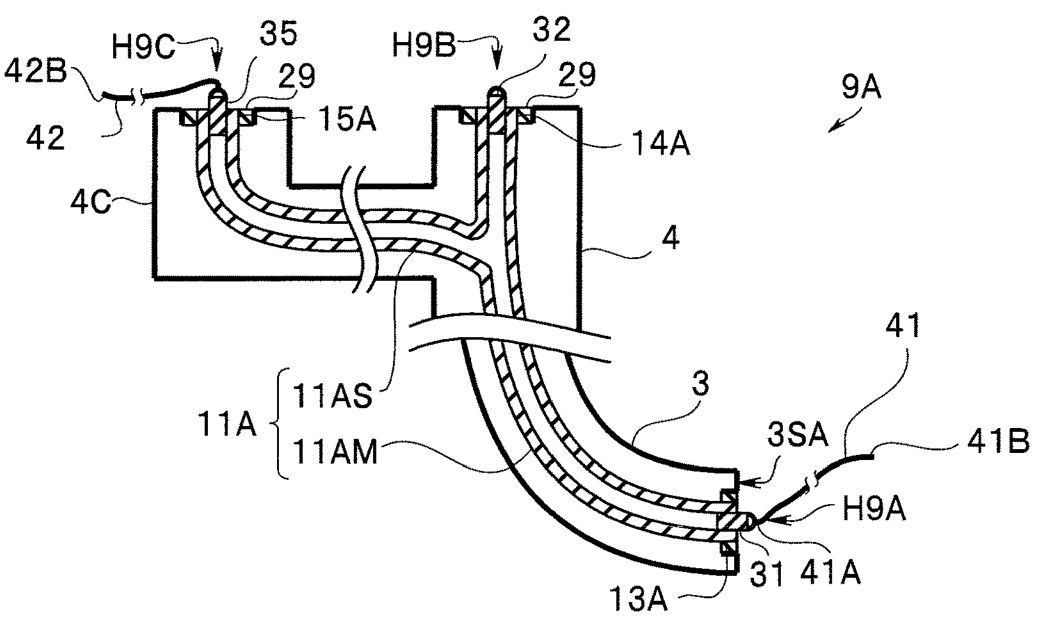
FIG. 17 is a schematic cross-sectional view for describing a replacement method of a channel according to the second embodiment.

As shown in FIG. 17, in the first channel 11A, the first plug 31 is arranged at the first distal end 13A, the second plug 32 is arranged at the second rear end 14B, and a third plug 35 is arranged at a first branch end 15A. A flow path of the first channel 11A is sealed by the three plugs 31, 32, and 35. The first channel 11A includes the first main channel 11M and the first subchannel 11S, the first channel 11M includes the first distal end 13A and the first rear end 14A, and the first subchannel 11S branching from a middle of the first main channel 11M and including the first branch end 15A.

Although not illustrated, in the second channel 11B, a plug 31B is arranged at the second distal end 13B and a plug 35B is arranged at a second branch end 15B. A plug 32B may also be arranged at the second rear end 14B. The second channel 11B includes a second main channel and a second subchannel, the second main channel 11B including the second distal 13B end and the second rear end 14B, and the second subchannel branching from a middle of the second main channel and including the second branch end 15B.

<Step S21> Release of Fixation of First Channel

Fixation of the first channel 11A is released in a similar manner to step S20 in FIG. 6. In the endoscope 9A, the fixing member 29 fixing the first branch end 15A of the first channel 11A to a branch opening (third opening) H9C of the connector 4C is, for example, also grinded off.

<Step S23> Connection of String

As shown in FIG. 17, a first string 41 includes a first end 41A and a second end 41B. A second string 42 includes a third end 42A and a fourth end 42B.

The channel replacement method includes sealing the flow path of the first channel 11A by arranging the third plug 35 at the first branch end 15A, connecting a first line 41 to the first plug 31 and connecting a second line 42 to the third plug 35. The channel includes the subchannel 11S that branches from the main channel 11M in the operation portion 4, and the subchannel 11S includes the first branch end 15A located in the third opening H9C of the connector 4C. The endoscope can include one or more of the first plug 31 arranged at the distal end 13A of the main channel 11M, the second plug 32 arranged at the rear end 14A of the main channel 11M, and the third plug 35 arranged at the first branch end 15A of the subchannel 11S. Each of the first plug 31, the second plug 32, and the third plug 35 includes an adhesive for fixing each of the first plug 31, the second plug 32, and the third plug 35 to the channel 11.

The first end 41A of the first string 41 is connected to the first plug 31, and the third end 42A of the second string 42 is connected to the third plug 35. A length of the first string 41 is longer than a main channel 11MA. A length of the second string 42 is longer than a subchannel 11SA.

<Step S36> Withdrawal of First Channel/Placement of String

Figure 18:
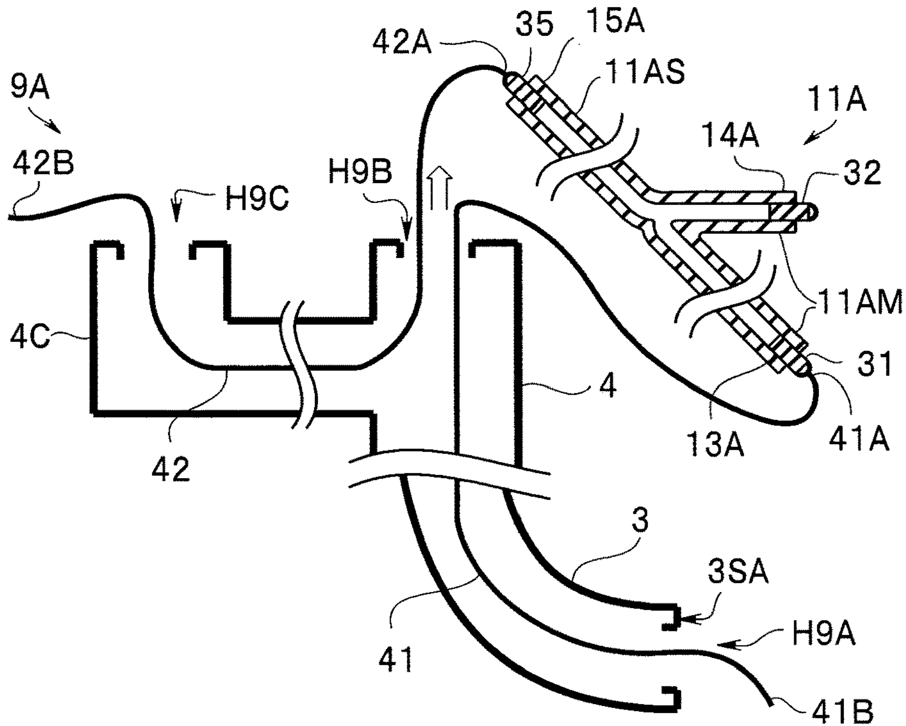
FIG. 18 is a schematic cross-sectional view for describing the replacement method of a channel according to the second embodiment.

As shown in FIG. 18, the first channel 11A is withdrawn from inside the endoscope 9A via the insertion opening H9B. When the first channel 11A is withdrawn, the first string 41 and the second string 42 are placed inside the endoscope 9A. In other words, a state is created where the first end 41A and the second end 41B of the first string 41 and the third end 42A and the fourth end 42B of the second string 42 are positioned outside of the endoscope 9A. The channel replacement method includes positioning the first line 41 and the second line 42 inside the endoscope 9 by withdrawing the first channel 11A via the insertion opening H9B where the first rear end 14A is arranged.

<Step S37> Connection of String to Second Channel

The first string 41 and the second string 42 are detached from the first channel 11A.

Figure 19:
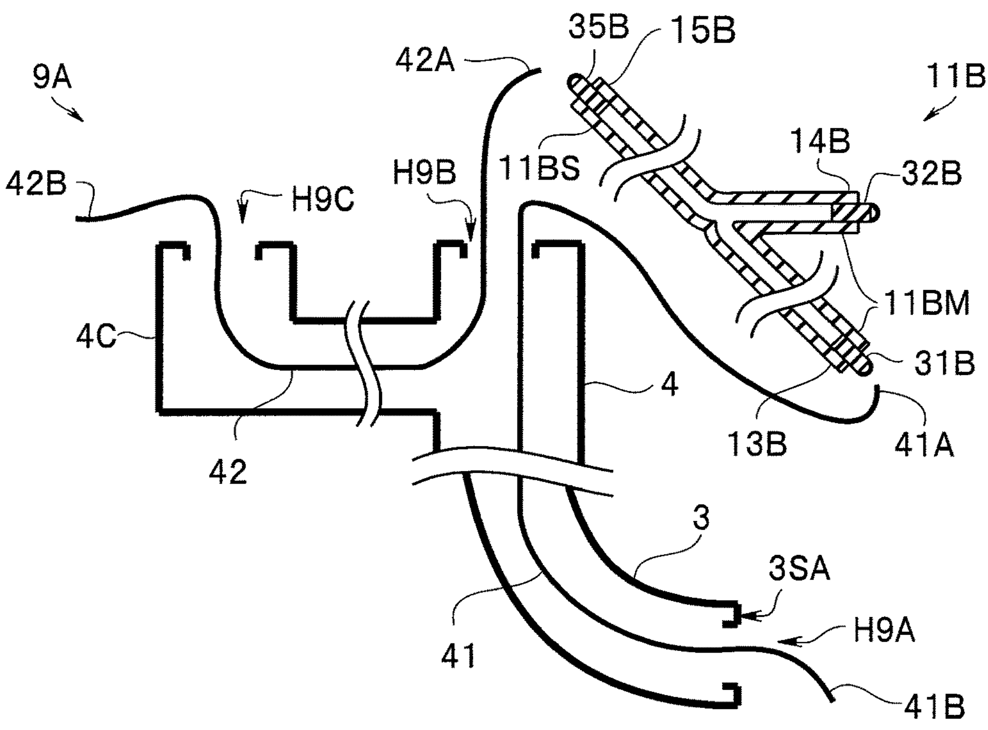
FIG. 19 is a schematic cross-sectional view for describing the replacement method of a channel according to the second embodiment.

As shown in FIG. 19, the first end 41A of the first string 41 is connected to the first plug 31B of the second channel 11B and the third end 42A of the second string 42 is connected to the third plug 35B.

<Step S41> Pulling of String, Insertion of Second Channel

Figure 20:
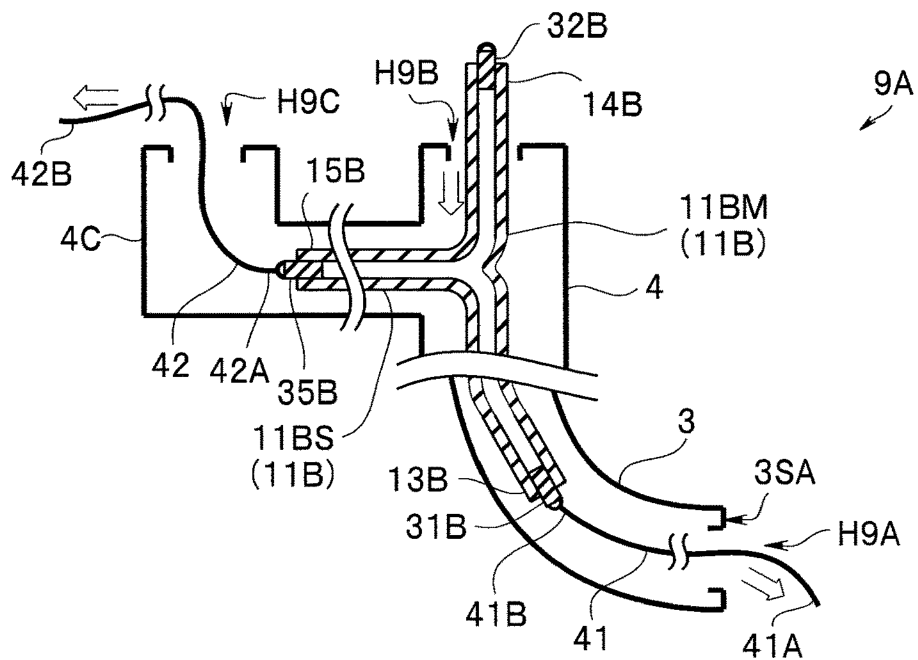
FIG. 20 is a schematic cross-sectional view for describing the replacement method of a channel according to the second embodiment.

As shown in FIG. 20, by pulling the second end 41B of the first string 41 and the fourth end 42B of the second string 42, the second channel 11B is inserted into the endoscope 9A via the insertion opening H9B. The channel replacement method includes connecting the first line 41 to the second distal end 13B and connecting the second line 42 to the second branch end 15B, and inserting the second channel 11B into the endoscope 9 via the insertion opening H9B by pulling the first line 41 connected to the second distal end 13B and the second line 42 connected to the second branch end 15B. The main channel 11M can extend or be inserted from the insertion portion 3 to the operation portion 4, and the subchannel 11S can extend or be inserted from the operation portion 3 to the connector 4C.

<Step S51> Fixation of Second Channel

The second channel 11B is fixed to the endoscope 9A in a similar manner to step S50 in FIG. 6. In the endoscope 9A, the second branch end 15B of the second channel 11B is also fixed to the branch opening H9C.

According to the channel replacement method of the present embodiment, even with the endoscope 9A in which the channel 11 includes a branch, the channel can be efficiently replaced without having to disassemble the endoscope.

Figure 21A:
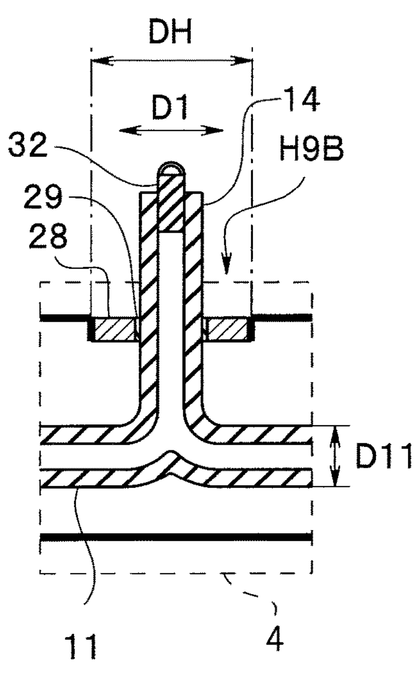
FIG. 21A is a schematic cross-sectional view of an operation portion opening according to the second embodiment.
Figure 21A:

In the endoscope 9A, the first channel 11A is withdrawn and the second channel 11B is inserted via the insertion opening H9B. Therefore, as shown in FIG. 21A, a size DH (for example, an inner diameter of the opening) of the insertion opening H9B is set larger than a size D1 (inner diameter) which enables the main channel 11M (outer diameter D11) to be inserted.

Therefore, the endoscope 9A can include a ring-shaped member 28 which fills a gap between the large insertion opening H9B and the channel 11. By using the ring-shaped member 28 in addition to an adhesive as the fixing member 29, the channel 11 can be readily fixed to the endoscope 9A with only a small amount of the adhesive. The ring-shaped member 28 is located in the gap between the second opening H9B and the rear end of the main channel 11M. The fixing member 29 attaches the channel 11 to the opening of the insertion portion 3.

Figure 21B:
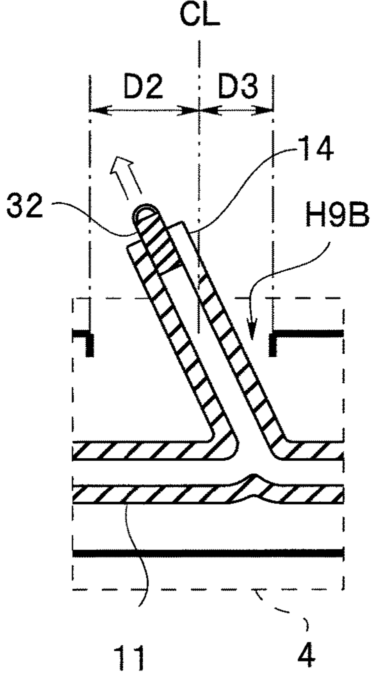
FIG. 21B is a schematic cross-sectional view of the operation portion opening according to the second embodiment.
Figure 21C:
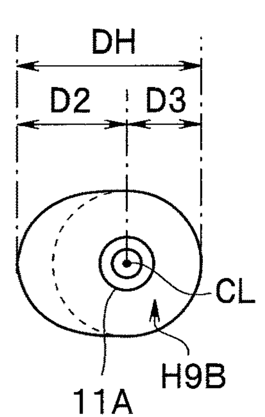
FIG. 21C is a top view of the operation portion opening according to the second embodiment.

As shown in FIG. 21B, when the channel 11 is extended from a branch portion in an inclined state, the insertion opening H9B can be given a non-circular shape including a long axis in a direction where the channel 11 is withdrawn as shown in FIG. 21C.

In other words, the insertion opening H9B shown in FIGS. 21B and 21C has an approximately elliptical shape of which a dimension D2 in a direction of withdrawal is larger than a dimension D3 in a direction opposite to the direction of withdrawal relative to an arrangement center CL where the channel 11 intersects with the opening. A shape of the second opening H9B is based on a direction in which the channel 11 is withdrawn.

The non-circular insertion opening H9B enables the channel 11 including the branch portion to be readily withdrawn.

Modification of Second Embodiment

An endoscope 9B according to the present modification is similar to the endoscope 9A according to the second embodiment and produces a same effect. Therefore, in the following description, components with same functions as the endoscope 9A will be assigned same reference signs and descriptions of such components will be omitted.

Figure 22:
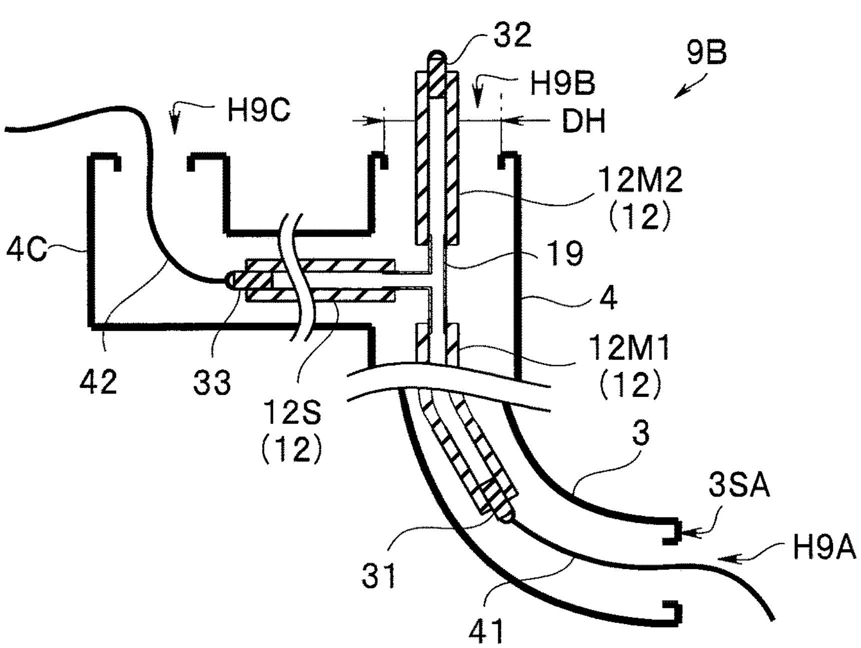
FIG. 22 is a schematic cross-sectional view of a channel of an endoscope according to a modification of the second embodiment.

As shown in FIG. 22, in the endoscope 9B according to the present modification, a channel 12 includes a T-shaped tube 19 which connects a main channel 12M and a subchannel 12S to each other in the operation portion 4. The main channel 12M is made up of a first main channel 12M1 from the projection opening H9A to the T-shaped tube 19 and a second main channel 12M2 from the T-shaped tube 19 to the insertion opening H9B. In the operation portion 4, the branch tube 19 connects the main channel (12M1, 12M2) and the subchannel 12S to each other. And the second opening H9B is large enough to enable the branch tube 19 to be withdrawn to the outside.

The channel 12 including the T-shaped tube 19 includes a branch but is readily manufactured.

The channel 12 of the endoscope 9B can be replaced by a same method as the channel 11 of the endoscope 9A. Therefore, an opening dimension DH of the insertion opening H9B of the endoscope 9B is set so that the channel 12 including the T-shaped tube 19 can be withdrawn and inserted via the insertion opening H9B.

Note that while the endoscopes 9 and 9A are flexible endoscopes for medical use, an endoscope according to another embodiment may be an endoscope for industrial use or a rigid endoscope including a rigid straight tube instead of a flexible portion 9C.

The present disclosure is not limited to the embodiments described above. Various modifications, alterations, and the like are possible within the scope of the gist of the present disclosure.

Example 1. A channel replacement method of replacing a first channel arranged inside an endoscope with a second channel,
- the first channel including a first distal end and a first rear end, the second channel including a second distal end and a second rear end, the channel replacement method comprising:
- sealing a flow path of the first channel by arranging a first plug at the first distal end and arranging a second plug at the first rear end,
- withdrawing the first channel from inside the endoscope, and
- inserting the second channel into the endoscope.

Example 2. The channel replacement method according to Example 1, comprising:
- mechanically connecting the first rear end and the second distal end or the first distal end and the second rear end to each other; and
- inserting the second channel into the endoscope by withdrawing the first channel from inside the endoscope.

Example 3. The channel replacement method according to Example 1, wherein
- a string is connected to the first plug or the second plug, the channel replacement method comprising:
- placing the string inside the endoscope by withdrawing the first channel from inside the endoscope; and
- inserting the second channel into the endoscope by pulling the string connected to the second distal end or the second rear end.

Example 4. The channel replacement method according to Example 1, wherein
- the first channel includes a first main channel which includes the first distal end and the first rear end and a first subchannel which branches from a middle of the first main channel and which includes a first branch end,
- the second channel includes a second main channel which includes the second distal end and the second rear end and a second subchannel which branches from a middle of the second main channel and which includes a second branch end, the channel replacement method comprising:
- sealing a flow path of the first channel by also arranging a third plug at the first branch end;
- connecting a first string to the first plug and connecting a second string to the third plug;
- placing the first string and the second string inside the endoscope by withdrawing the first channel via an insertion opening where the first rear end is arranged; and
- inserting the second channel into the endoscope via the insertion opening by pulling the first string connected to the second distal end and the second string connected to the second branch end.

Example 5. An endoscope, comprising:
- an insertion portion;
- an operation portion arranged at a proximal end of the insertion portion;
- a universal cord extended from the operation portion;
- a connector arranged at a proximal end of the universal cord; and
- a channel including a main channel which includes a distal end in a projection opening of the insertion portion and a rear end in an insertion opening of the operation portion and which is inserted from the insertion portion to the operation portion, and a subchannel which branches from the main channel in the operation portion, which includes a branch end in a branch opening of the connector, and which is inserted from the operation portion to the connector, wherein
- the insertion opening is large enough to enable the channel to be withdrawn to an outside via the insertion opening.

Example 6. The endoscope according to Example 5, comprising
- a ring-shaped member arranged in a gap between the insertion opening and the rear end of the main channel.

Example 7. The endoscope according to Example 5, wherein
- a shape of the insertion opening is set based on a direction in which the channel is withdrawn.

Example 8. The endoscope according to Example 5, comprising
- in the operation portion, a T-shaped tube connecting the main channel and the subchannel to each other, wherein
- the insertion opening is large enough to enable the T-shaped tube to be withdrawn to the outside.

Example 9. The endoscope according to Example 5, comprising
- a first plug arranged at the distal end, a second plug arranged at the rear end, and a third plug arranged at the branch end.

Example 10. The endoscope according to Example 9, wherein each of the first plug, the second plug, and the third plug includes an adhesive for fixing each of the first plug, the second plug, and the third plug to the channel.

Example 11. The endoscope according to Example 5, wherein the endoscope is a single-use endoscope which is disposed of after a single use.

Example 12. A plug which stops up an opening of a channel of an endoscope, wherein the plug includes an adhesive for fixing the plug to the opening.

Example 13. A channel withdrawal method, wherein a channel arranged inside an endoscope includes a first distal end and a first rear end, the channel withdrawal method comprising:

sealing a flow path of the channel by arranging a plug at the first distal end and arranging a second plug at the first rear end; and withdrawing the channel from inside the endoscope.

What is claimed is:

1. A channel replacement method to replace a first channel of an endoscope, the first channel including a first distal end and a first rear end, the channel replacement method comprising:

sealing a flow path of the first channel by arranging a first plug at the first distal end and arranging a second plug at the first rear end; and withdrawing the first channel from inside the endoscope, wherein withdrawing the first channel from inside the endoscope includes:

withdrawing the first channel from a rear side of an insertion portion toward a distal side of the insertion portion.

2. The channel replacement method according to claim 1, wherein a fixing member attaches the first channel to a first opening of an insertion portion of the endoscope, and wherein the method further comprises removing the fixing member before withdrawing the first channel from inside the endoscope.

3. The channel replacement method according to claim 1, further comprising:

after withdrawing the first channel, inserting a second channel into the endoscope such that the second channel occupies a space within the endoscope previously occupied by the first channel, wherein the second channel includes a second distal end and a second rear end.

4. The channel replacement method according to claim 3, wherein the first channel includes a first main channel and a first subchannel, the first channel including the first distal end and the first rear end, and the first subchannel branching from a middle of the first main channel and including a first branch end, wherein the second channel includes a second main channel and a second subchannel, the second main channel including the second distal end and the second rear end, and the second subchannel branching from a middle of the second main channel and including a second branch end, wherein the channel replacement method further comprises:

sealing the flow path of the first channel by arranging a third plug at the first branch end;

connecting a first line to the first plug and connecting a second line to the third plug; and positioning the first line and the second line inside the endoscope by withdrawing the first channel via a second opening where the first rear end is arranged.

5. The channel replacement method according to claim 4, wherein the channel replacement method further comprises:

connecting the first line to the second distal end and connecting the second line to the second branch end; and inserting the second channel into the endoscope via the second opening by pulling the first line connected to the second distal end and the second line connected to the second branch end.

6. The channel replacement method according to claim 3, wherein inserting the second channel into the endoscope includes inserting the second channel into the endoscope from a rear side of an insertion portion of the endoscope toward a distal side of the insertion portion.

7. The channel replacement method according to claim 3, further comprising:

fixing the second channel to the endoscope.

8. The channel replacement method according to claim 7, wherein fixing the second channel to the endoscope includes:

fixing a rear end of the second channel to the endoscope and a distal end of the second channel to the endoscope, wherein the rear end and the distal end are fixed using different fixing member.

9. The channel replacement method according to claim 1, further comprising:

after withdrawing the first channel, inserting a second channel into the endoscope such that the second channel occupies a space within the endoscope previously occupied by the first channel, wherein the second channel includes a second distal end and a second rear end;

connecting a line to the first plug or the second plug;

positioning the line inside the endoscope by withdrawing the first channel from inside the endoscope;

connecting the line to the second distal end or the second rear end of the second channel; and inserting the second channel into the endoscope by pulling the line connected to the second distal end or the second rear end.

10. The channel replacement method according to claim 1, further comprising:

releasing a fixation of the first channel to the endoscope.

11. The channel replacement method according to claim 10, wherein the releasing the fixation of the first channel to the endoscope is performed before the withdrawing the first channel from inside the endoscope.

12. The channel replacement method according to claim 1, further comprising:

after withdrawing the first channel, inserting a second channel into the endoscope such that the second channel occupies a space within the endoscope previously occupied by the first channel from the rear side of an insertion portion toward the distal side of the insertion portion.

13. The channel replacement method according to claim 1, wherein sealing the flow path of the first channel includes:

preventing from flowing out during withdrawing the first channel from inside the endoscope.

14. A channel replacement method to replace a first channel of an endoscope, the first channel including a first distal end and a first rear end, the channel replacement method comprising:

sealing a flow path of the first channel by arranging a first plug at the first distal end and arranging a second plug at the first rear end;

withdrawing the first channel from inside the endoscope; and after withdrawing the first channel, inserting a second channel into the endoscope such that the second channel occupies a space within the endoscope previously occupied by the first channel, wherein the second channel includes a second distal end and a second rear end, wherein withdrawing the first channel from inside the endoscope and inserting the second channel into the endoscope includes:

mechanically connecting the first rear end and the second distal end or the first distal end and the second rear end to each other; and inserting the second channel into the endoscope by withdrawing the first channel from inside the endoscope.

15. A channel replacement method to replace a first channel of an endoscope, the first channel including a first distal end and a first rear end, the channel replacement method comprising:

sealing a flow path of the first channel by arranging a first plug at the first distal end and arranging a second plug at the first rear end;

withdrawing the first channel from inside the endoscope;

sealing a flow path of a second channel by arranging a third plug at a rear end of the second channel; and connecting the first plug and the third plug.

16. The channel replacement method according to claim 15, wherein connecting the first plug and the third plug is performed while the first channel is fixed to the endoscope.

17. The channel replacement method according to claim 15, further comprising:

releasing a fixation of the first channel to the endoscope while the first channel is fixed to the endoscope.

18. The channel replacement method according to claim 15, further comprising:

sealing the flow path of the second channel by arranging a fourth plug at a distal end of the second channel.

19. The channel replacement method according to claim 15, wherein sealing the flow path of the second channel includes:

preventing from contaminating the second channel during withdrawing the first channel from inside the endoscope.

* * * * *